(12) United States Patent
Yeung

(10) Patent No.: US 9,096,580 B2
(45) Date of Patent: Aug. 4, 2015

(54) BENZOFURAN DERIVATIVES FOR THE TREATMENT OF HEPATITIS C

(71) Applicant: BRISTOL-MYERS SQUIBB COMPANY, Princeton, NJ (US)

(72) Inventor: Kap-Sun Yeung, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/387,883

(22) PCT Filed: Mar. 26, 2013

(86) PCT No.: PCT/US2013/033790
§ 371 (c)(1),
(2) Date: Sep. 25, 2014

(87) PCT Pub. No.: WO2013/148620
PCT Pub. Date: Oct. 3, 2013

(65) Prior Publication Data
US 2015/0141395 A1   May 21, 2015

Related U.S. Application Data

(60) Provisional application No. 61/615,971, filed on Mar. 27, 2012.

(51) Int. Cl.
*A61K 31/506* (2006.01)
*C07D 405/14* (2006.01)
*A61K 45/06* (2006.01)

(52) U.S. Cl.
CPC ............ *C07D 405/14* (2013.01); *A61K 31/506* (2013.01); *A61K 45/06* (2013.01)

(58) Field of Classification Search
USPC ................ 514/210.2, 256; 544/333; 548/953
See application file for complete search history.

(56) References Cited

U.S. PATENT DOCUMENTS

| 7,994,171 | B2 | 8/2011 | Yeung et al. |
| 8,048,887 | B2 | 11/2011 | Yeung et al. |
| 8,148,382 | B2 | 4/2012 | Yeung et al. |
| 8,198,449 | B2 | 6/2012 | Pracitto et al. |
| 8,293,909 | B2 | 10/2012 | Pracitto et al. |
| 8,309,558 | B2 | 11/2012 | Yeung et al. |
| 8,536,338 | B2 | 9/2013 | Pracitto et al. |
| 8,722,688 | B2 | 5/2014 | Yeung et al. |
| 2012/0316126 | A1 | 12/2012 | Yeung et al. |

FOREIGN PATENT DOCUMENTS

| WO | WO 2011/112191 | 9/2011 |
| WO | WO 2012/078545 | 6/2012 |

*Primary Examiner* — Kristin Vajda
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

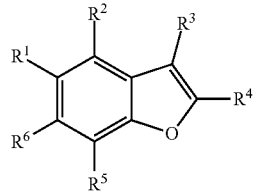

12 Claims, No Drawings

BENZOFURAN DERIVATIVES FOR THE TREATMENT OF HEPATITIS C

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed, see for example, WO2009/101022.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The present invention relates to compounds having the Formula I, their pharmaceutical formulations, and use in treating hepatitis C.

One aspect of the invention is a compound of formula I

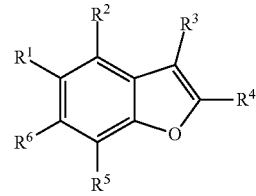

where:
$R^1$ is phenyl or pyridinyl and is substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy, and wherein the phenyl or pyridinyl is also substituted with 1 $CON(R^9)(R^{10})$ substituent;
$R^2$ is hydrogen, halo, alkyl, or alkoxy;
$R^3$ is cyano, alkoxycarbonyl, (cycloalkyl)oxycarbonyl, (alkylsulfonyl)aminocarbonyl, $CON(R^{13})(R^{14})$, $(R^{13})(R^{14})$NCONH, thiazolyl, tetrazolyl, triazolyl, or imidazolyl wherein the thiazolyl, tetrazolyl, triazolyl, or imidazolyl is substituted with 0-3 halo or alkyl substituents;
$R^4$ is phenyl that is independently substituted with 0-2 halo, alkyl, or alkoxy or is para substituted with X—Ar$^1$;
$R^5$ and $R^6$ are independently hydrogen, nitro, halo, alkyl, alkoxy, $N(R^7)(R^8)$, or alkylsulfonyl;
$R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, alkylsulfonylalkyl, $SO_2N(R^{15})(R^{16})$, or benzyl where said benzyl is substituted with 0-3 substituents selected from halo, alkyl, haloalkyl, alkoxy, haloalkoxy, carboxy, and alkoxycarbonyl;

or N(R$^7$)(R$^8$) taken together is azetidinyl, pyrrolidinyl, piperidinyl, or piperazinyl, and is substituted with 0-2 substituents selected from alkyl, hydroxyalkyl, or hydroxy;
R$^9$ is

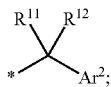

R$^{10}$ is hydrogen;
R$^{11}$ and R$^{12}$ taken together with the carbon to which they are attached is azetidinyl substituted with 0-3 alkyl substituents;
R$^{13}$ is hydrogen or alkyl;
R$^{14}$ is hydrogen or alkyl;
R$^{15}$ is hydrogen or alkyl;
R$^{16}$ is hydrogen or alkyl;
X is —O— or —NH—;
Ar$^1$ is phenyl or para-halophenyl; and
Ar$^2$ is phenyl, pyridinyl, pyrazinyl, pyrimidinyl, pyrazolyl, isoxazolyl, imidazolyl, oxazolyl, thiazolyl, oxadiazolyl, oxadiathiazolyl, triazolyl, or tetrazolyl, and is substituted with 0-3 substituents selected from halo, alkyl, or dialkylamino;
or a pharmaceutically acceptable salt thereof.

Another aspect of the invention is a compound of formula I where
where R$^1$ is phenyl substituted with 0-3 substituents selected from the group consisting of halo and alkoxy, and is also substituted with 1 CON(R$^9$)(R$^1$) substituent;
R$^2$ is hydrogen or halo;
R$^3$ is CON(R$^{13}$)(R$^{14}$);
R$^4$ is phenyl that is para substituted with halo;
R$^5$ is hydrogen;
R$^6$ is hydrogen, nitro, halo, alkyl, alkoxy, N(R$^7$)(R$^8$), or alkylsulfonyl;
Ar$^2$ is phenyl, pyridinyl, or pyrimidinyl, and is substituted with 0-3 substituents selected from halo or alkyl;
or a pharmaceutically acceptable salt thereof Another aspect of the invention is a compound of formula I wherein R$^1$ is phenyl substituted with 2 substituents selected from the group consisting of halo, alkyl, and alkoxy, and is also substituted with 1 CON(R$^9$)(R$^{10}$) substituent; R$^2$ is halo; R$^3$ is CONHMe; R$^4$ is phenyl that is para substituted with halo; R$^5$ is hydrogen; R$^6$ is hydrogen; and Ar$^2$ is pyrimidinyl; or a pharmaceutically acceptable salt thereof.

Another aspect of the invention is a compound of formula I where R$^1$ is phenyl or pyridinyl wherein the phenyl or pyridinyl is substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy, and is also substituted with 1 CON(R$^9$)(R$^{10}$) substituent; or a pharmaceutically acceptable salt thereof Another aspect of the invention is a compound of formula I where R$^2$ is hydrogen, halo, alkyl, or alkoxy.

Another aspect of the invention is a compound of formula I where R$^2$ is hydrogen or halo.

Another aspect of the invention is a compound of formula I where R$^3$ is CON(R$^{13}$)(R$^{14}$).

Another aspect of the invention is a compound of formula I where R$^3$ is imidazolyl.

Another aspect of the invention is a compound of formula I where R$^3$ is imidazol-2-yl.

Another aspect of the invention is a compound of formula I where R$^4$ is phenyl that is independently substituted with 0-2 halo, alkyl, or alkoxy substituents or is para substituted with X—Ar$^1$.

Another aspect of the invention is a compound of formula I where R$^4$ is phenyl that is substituted with 0-1 halo substituent.

Another aspect of the invention is a compound of formula I where R$^5$ and R$^6$ are independently hydrogen, nitro, halo, alkyl, alkoxy, N(R$^7$)(R$^8$), or alkylsulfonyl.

Another aspect of the invention is a compound of formula I where R$^5$ is hydrogen and R$^6$ is hydrogen or N(R$^7$)(R$^8$).

Another aspect of the invention is a compound of formula I where R$^7$ and R$^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, alkylsulfonylalkyl, SO$_2$N(R$^{13}$)(R$^{14}$), or benzyl where said benzyl is substituted with 0-3 substituents selected from halo, alkyl, haloalkyl, alkoxy, haloalkoxy, carboxy, and alkoxycarbonyl.

Another aspect of the invention is a compound of formula I where N(R$^7$)(R$^8$) taken together is azetidinyl, pyrrolidinyl, piperidinyl, or piperazinyl, and is substituted with 0-2 substituents selected from alkyl, hydroxyalkyl, or hydroxyl.

Another aspect of the invention is a compound of formula I where R$^9$ is

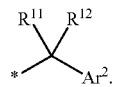

Another aspect of the invention is a compound of formula I where R$^{10}$ is hydrogen.

Another aspect of the invention is a compound of formula I where R$^{13}$ is hydrogen or alkyl.

Another aspect of the invention is a compound of formula I where R$^{14}$ is hydrogen or alkyl.

Another aspect of the invention is a compound of formula I where R$^{15}$ is hydrogen or alkyl.

Another aspect of the invention is a compound of formula I where R$^{16}$ is hydrogen or alkyl.

Another aspect of the invention is a compound of formula I where X is —O— or —NH—.

Another aspect of the invention is a compound of formula I where X is —O—.

Another aspect of the invention is a compound of formula I where Ar$^1$ is phenyl or para-halophenyl.

Another aspect of the invention is a compound of formula I where Ar$^2$ is phenyl, pyridinyl, pyrazinyl, pyrimidinyl, pyrazolyl, isoxazolyl, imidazolyl, oxazolyl, thiazolyl, oxadiazolyl, oxadiathiazolyl, triazolyl, or tetrazolyl, and is substituted with 0-3 substituents selected from halo, alkyl, or dialkylamino;

Another aspect of the invention is a compound of formula I where Ar$^2$ is phenyl, pyridinyl, pyrazinyl, or pyrimidinyl; or a pharmaceutically acceptable salt thereof Any scope of any variable, including R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, X, Ar$^1$, or Ar$^2$ can be used independently with the scope of any other instance of a variable.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." Ethylene means ethanediyl or —CH$_2$CH$_2$—; propylene means propanediyl or —CH$_2$CH$_2$CH$_2$—; butylene means butanediyl or —CH$_2$CH$_2$CH$_2$CH$_2$—; pentylene means pentanediyl or —CH$_2$CH$_2$CH$_2$CH$_2$CH$_2$—. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents R$^1$ and R$^2$ of formula IV are intended to bond to the benzene ring of formula IV and not to the thiophene ring.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 1.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |

TABLE 1-continued

| Brand Name | Physiological Class | Type of Inhibitor or Target | Source Company |
|---|---|---|---|
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |

TABLE 1-continued

| Brand Name | Physiological Class | Type of Inhibitor or Target | Source Company |
|---|---|---|---|
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |

TABLE 1-continued

| Brand Name | Physiological Class | Type of Inhibitor or Target | Source Company |
| --- | --- | --- | --- |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/ Bristol-Myers Squibb |

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "oc", "fl", "R", "S", "E", and "Z" are stereochemical designations familiar to one skilled in the art.

A route to prepare compounds of formula 1 is shown in Schemes 1.

Scheme 1.

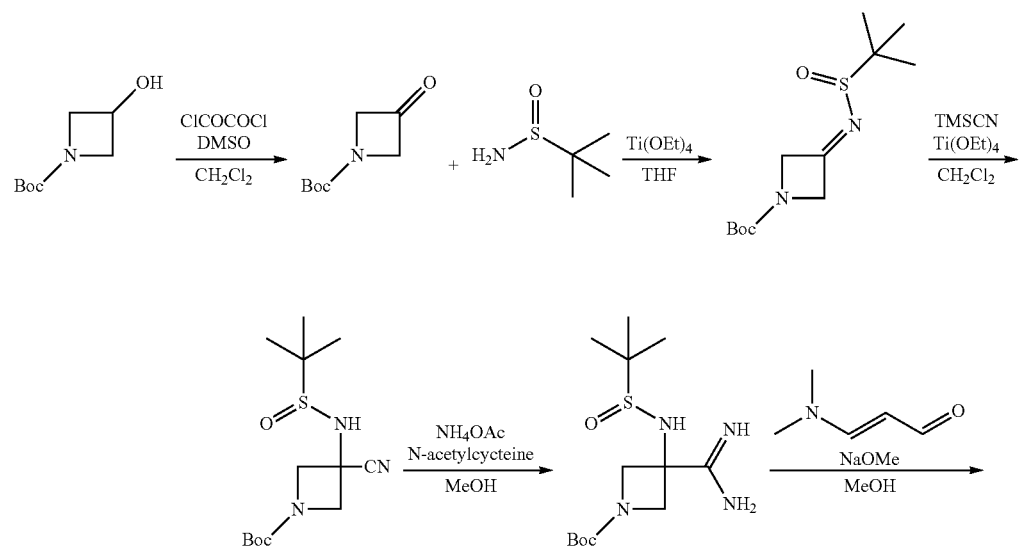

-continued

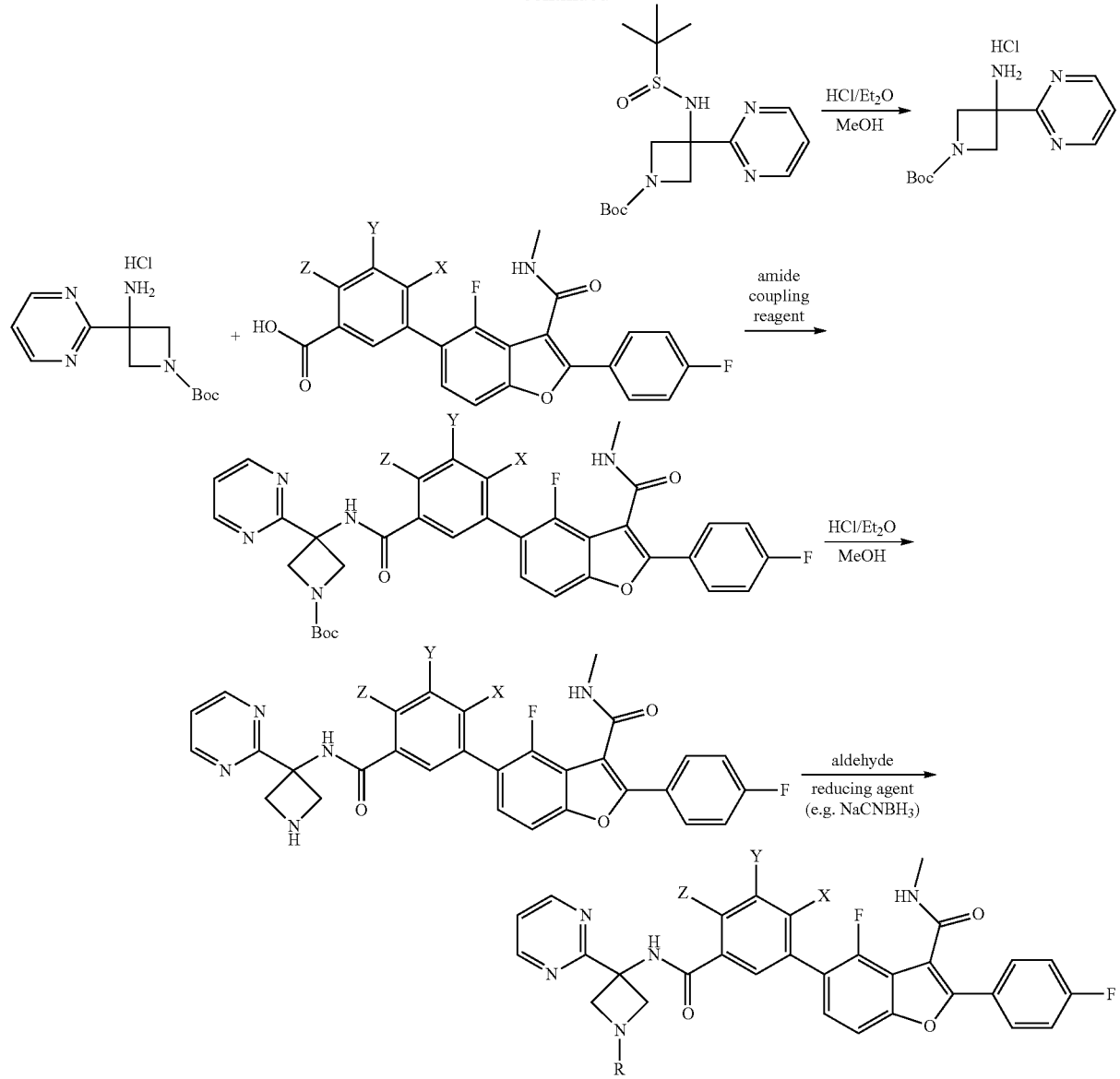

Preparation of tert-butyl 3-oxoazetidine-1-carboxylate

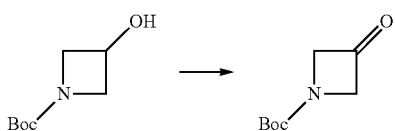 [SMILES: CC(C)(C)OC(=O)N1CC(O)C1 ; CC(C)(C)OC(=O)N1CC(=O)C1]

A mixture of oxalyl chloride (2.78 ml, 31.8 mmol) in CH$_2$Cl$_2$ (80 ml) in a 500 ml round-bottomed flask was cooled to −78° C., and DMSO (4.51 ml, 63.5 mmol) was added dropwise to the mixture over 15 min. The reaction mixture was then stirred at the same temperature for 15 min. A solution of tert-butyl 3-hydroxyazetidine-1-carboxylate (5 g, 28.9 mmol) in CH$_2$Cl$_2$ (50 ml) followed by a solution triethylamine (16.09 ml, 115 mmol) in CH$_2$Cl$_2$ (70 ml) were added dropwise to the reaction mixture. The reaction mixture was warmed to room temperature, and then stirred overnight. The reaction mixture was washed with brine, and the aqueous layer back extracted with CH$_2$Cl$_2$ (200 ml). The combined organic layers were washed with water, dried over Na$_2$SO$_4$, filtered and concentrated in vacuum to provide a crude mixture. The crude product was then purified by column chromatography (15% EtOAc in Hexane) to afford tert-butyl 3-oxoazetidine-1-carboxylate Yield: 4 g (81%). $^1$H NMR (400 MHz, CDCl$_3$): δ 4.69 (s, 4H), 1.49 (s, 9H).

Preparation of tert-butyl 3-(tert-butylsulfinylimino)azetidine-1-carboxylate

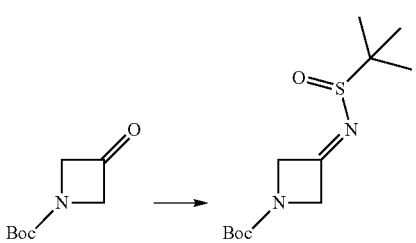 [SMILES: CC(C)(C)OC(=O)N1CC(=O)C1 ; CC(C)(C)OC(=O)N1CC(=NS(=O)C(C)(C)C)C1]

A mixture of tert-butyl 3-oxoazetidine-1-carboxylate (4 g, 23.37 mmol), 2-methylpropane-2-sulfinamide (3.12 g, 25.7 mmol) and tetraethoxytitanium (10.66 g, 46.7 mmol) in THF (40 ml) in a 20 ml sealed tube was stirred at 70° C. overnight. The reaction mixture was cooled to room temperature, quenched with water and filtered through a bed of Celite. The solid material was washed with ethyl acetate. The organic layer was separated, dried over Na$_2$SO$_4$, filtered and concentrated to obtain a crude mixture. The crude product was then purified by column chromatography (20% EtOAc in Hexane) to afford tert-butyl 3-(tert-butylsulfinylimino)azetidine-1-carboxylate Yield: 1.5 g (24%). $^1$H NMR (400 MHz, CDCl$_3$): δ 5.15-4.94 (m, 1H), 4.75 (m, 1H), 4.68 (s, 2H), 1.45 (s, 9H), 1.27 (s, 9H).

Preparation of tert-butyl 3-cyano-3-(1,1-dimethylethylsulfinamido)azetidine-1-carboxylate

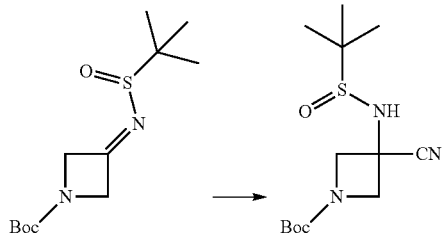 [SMILES: CC(C)(C)OC(=O)N1CC(=NS(=O)C(C)(C)C)C1 ; CC(C)(C)OC(=O)N1CC(C#N)(NS(=O)C(C)(C)C)C1]

To a mixture of tert-butyl 3-(tert-butylsulfinylimino)azetidine-1-carboxylate (1.5 g, 5.47 mmol) and Ti(OEt)$_4$ (2.494 g, 10.93 mmol) in CH$_2$Cl$_2$ (10 ml) under a nitrogen atmosphere in a 50 ml round-bottomed flask was added TMS-CN (1.83 ml, 13.67 mmol). The reaction mixture was stirred overnight and then quenched with water. The solid formed was filtered through a bed of Celite and washed with ethyl acetate. The organic layer was separated, dried over Na$_2$SO$_4$, filtered, and concentrated to give a crude mixture. The crude product was taken for next step without further purification. Yield: 1.5 g (91%). $^1$H NMR (400 MHz, CDCl$_3$): δ 4.49-4.35 (m, 2H), 4.14-4.4.11 (m, 2H), 1.45 (s, 9H), 1.27 (s, 9H). LCMS: (ES+) m/z observed=202.2 (M+H)$^+$ of N-(3-cyanoazetidin-3-yl)-2-methylpropane-2-sulfinamide. Column-Ascentis Express C18 (5×4 6 mm-5 μm).

Mobile phase A: 2% MeCN—98% H$_2$O—10 mM NH$_4$COOH

Mobile phase B: 98% MeCN—2% H$_2$O—10 mM NH$_4$COOH

Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RetentionTime min: 1.8, wavelength: 220 nm

Synthesis of tert-butyl 3-carbamimidoyl-3-(1,1-dimethylethylsulfinamido)azetidine-1-carboxylate

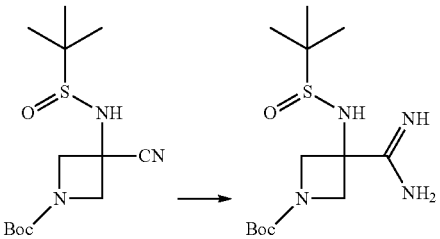 [SMILES: CC(C)(C)OC(=O)N1CC(C#N)(NS(=O)C(C)(C)C)C1 ; CC(C)(C)OC(=O)N1CC(NS(=O)C(C)(C)C)(C(=N)N)C1]

A mixture of (R)-2-acetamido-3-mercaptopropanoic acid (N-acetylcycteine, 0.812 g, 4.98 mmol), tert-butyl 3-cyano-3-(1,1-dimethylethylsulfinamido)azetidine-1-carboxylate (1.5 g, 4.98 mmol), and ammonium acetate (1.918 g, 24.88 mmol) in MeOH (5 ml) in a 15 ml sealed tube was heated at 70° C. overnight. Analysis of the reaction mixture by LCMS showed 38% desired product with other impurities but no starting material present. The reaction mixture was used for the next step without workup.

LCMS: (ES+) m/z=319.2 (M+H)$^+$

Column-Ascentis Express C18 (5×4 6 mm-5 μm)

Mphase A: 2% MeCN—98% H$_2$O—10 mM NH$_4$COOH

Mphase B: 98% MeCN—2% H$_2$O—10 mM NH$_4$COOH

Flow: 1 ml/Min

| Time | % A | % B |
|---|---|---|
| 0.0 | 100.0 | 0 |
| 1.5 | 0.0 | 100.0 |
| 3.2 | 0.0 | 100.0 |

RT min: 1.59, wavelength: 220 nm

Preparation of tert-butyl-3-(1,1-dimethylethylsulfinamido)-3-(pyrimidin-2-yl)azetidine-1-carboxylate

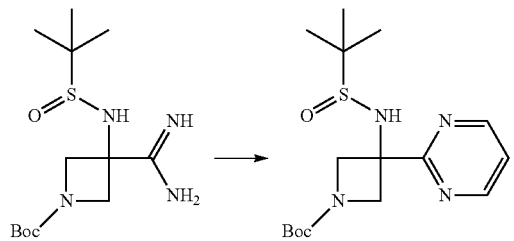 [SMILES: CC(C)(C)OC(=O)N1CC(NS(=O)C(C)(C)C)(C(=N)N)C1 ; CC(C)(C)OC(=O)N1CC(NS(=O)C(C)(C)C)(c2ncccn2)C1]

To the above reaction mixture of tert-butyl 3-carbamimidoyl-3-(1,1-dimethylethylsulfinamido)azetidine-1-carboxylate (assumed 4.98 mmol) in methanol (5 mL) was added sodium methoxide (0.509 g, 9.42 mmol) and (E)-3-(dimethylamino)acrylaldehyde (0.560 g, 5.65 mmol), and the resulting solution was heated at 70° C. overnight. The reaction mixture was then concentrated and the residue dissolved in ethyl acetate. The mixture was washed with water followed by saturated brine solution, and then dried over Na$_2$SO$_4$ and concentrated. The crude product was then purified by column chromatography (50% EtOAc in Hexane) to afford tert-butyl 3-(1,1-dimethylethylsulfinamido)-3-(pyrimidin-2-yl)azetidine-1-carboxylate Yield: 200 mg (overall 12%). ¹H NMR (400 MHz, CDCl₃): δ 8.78 (d, J=4.8 Hz, 2H), 7.24 (m, 1H), 4.63-4.48 (m, 2H), 4.23 (d, J=9.2 Hz, 2H), 1.47 (s, 9H), 1.29 (s, 9H). LCMS: (ES+) m/z observed=255.2 (M+H)⁺ of 2-methyl-N-(3-(pyrimidin-2-yl)azetidin-3-yl)propane-2-sulfinamide.

Column-Ascentis Express C18 (5×4 6 mm-5 μm)
Mphase A: 2% MeCN—98% H₂O—10 mM NH₄COOH
Mphase B: 98% MeCN—2% H₂O—10 mM NH₄COOH
Flow: 1 ml/Min

| Time | % A | % B |
|------|-----|-----|
| 0.0 | 100.0 | 0 |
| 1.5 | 0.0 | 100.0 |
| 3.2 | 0.0 | 100.0 |

RT min: 1.69, wavelength: 220 nm

Preparation of tert-butyl 3-amino-3-(pyrimidin-2-yl)azetidine-1-carboxylate hydrochloride

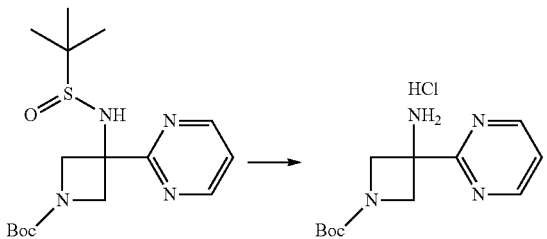 [SMILES: CC(C)(C)OC(=O)N1CC(NS(=O)C(C)(C)C)(c2ncccn2)C1 ; CC(C)(C)OC(=O)N1CC(N)(c2ncccn2)C1 ; Cl]

tert-Butyl 3-(1,1-dimethylethylsulfinamido)-3-(pyrimidin-2-yl)azetidine-1-carboxylate (40 mg, 0.113 mmol) in MeOH (0.5 ml) in a 10 ml round-bottomed flask was cooled to 0° C. A solution of HCl in ether (0.141 ml, 0.564 mmol, 4 N) was added. The mixture was then stirred at 0° C. for 15 min and then concentrated at room temperature. The residue was triturated with hexane and diethyl ether. The resulting solid was allowed to settle and supernatant liquid was decanted. The solid obtained was dried under vacuo to afford tert-butyl 3-amino-3-(pyrimidin-2-yl)azetidine-1-carboxylate hydrochloride Yield: 28 mg (87%). ¹H NMR (400 MHz, DMSO-d₆): δ 9.08 (bs, 2H), 9.0 (d, J=4.8 Hz, 2H), 7.63 (t, J=4.8 Hz, 1H), 4.23-4.21 (m, 4H), 1.43 (s, 9H). LCMS: (ES+) m/z observed=151.2 (M+H)⁺ of 3-(pyrimidin-2-yl)azetidin-3-amine Column-Ascentis Express C18 (5×4 6 mm-5 μm)
Mphase A: 2% MeCN—98% H₂O—10 mM NH₄COOH
Mphase B: 98% MeCN—2% H₂O—10 mM NH₄COOH
Flow: 1 ml/Min

| Time | % A | % B |
|------|-----|-----|
| 0.0 | 100.0 | 0 |
| 1.5 | 0.0 | 100.0 |
| 3.2 | 0.0 | 100.0 |

RT min: 1.49, wavelength: 220 nm

Preparation of ethyl 4-fluoro-2-(4-fluorophenyl)-5-hydroxybenzofuran-3-carboxylate

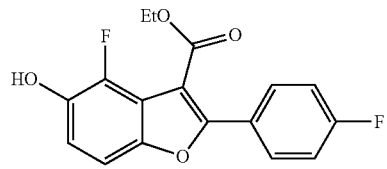 [SMILES: CCOC(=O)c1c(-c2ccc(F)cc2)oc2ccc(O)c(F)c12]

To a mixture of ethyl 2-(4-fluorophenyl)-5-hydroxybenzofuran-3-carboxylate (500 mg, 1.665 mmol) in acetonitrile (10 mL) at r.t. under N₂ was added 1-(chloromethyl)-4-fluoro-1,4-diazoniabicyclo[2.2.2]octane tetrafluoroborate (708 mg, 1.998 mmol). The mixture was stirred at r.t. (the mixture turned bright yellow in color) for 20 hours. The mixture was evaporated. The residue was added with 10 ml H₂O. The aqueous decanted, and the residue further washed with 2×5 ml H₂O. The mixture was dissolved in MeOH (about 10 ml), and the insoluble filtered. The filtrate was purified by Shimadzu-VP preparative reverse phase HPLC using the separation method: Solvent A=10% MeOH-90% H₂O—0.1% TFA, Solvent B=90% MeOH-10% H₂O—0.1% TFA, Start % B=60, Final % B=100, Gradient time=10 min, Stop time=12 min, Flow Rate=25 mL/min, Column: Waters-Sunfire 19×100 mm S5, Fraction Collection: 6.44-7.24 min. (UV detection at 220 nm). The desired fractions were combined and evaporated to give a yellow solid. The yellow solid was further purified by Biotage Horizon flash chromatography (0 to 70% EtOAc/Hexane, 3×80 g silica gel column) to give a light yellow solid (108.9 mg). ¹H NMR (500 MHz, CD₃OD) δ 7.95 (m, 2H), 7.26 (t overlapping with dd, 2H), 7.25 (dd, 1H), 7.03 (t, J=8.39, 1H), 4.39 (q, J=7.17, 2H), 1.36 (t, J=7.17, 3H). ¹⁹F NMR (470.45 MHz, CD₃OD) δ −112.36, −142.29 (The ¹⁹F chemical shift was referenced to CFCl₃ at 0.0 ppm). The position of the F atom at C4 was confirmed by ¹H-¹H through bond correlation between H6 and H7, ¹H-¹³C HMBC and F-C4 coupling in ¹³C NMR (125.75 MHz, CD₃OD) (δ 144.8 ppm, d, J=247, C4). LC/MS were performed by using Shimadzu-VP instrument with UV detection at 220 nm and Waters Micromass. HPLC method: Solvent A=10% MeOH-90% H₂O—0.1% TFA, Solvent B=90% MeOH-10% H₂O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=319.14, HPLC R_t=1.718 min. The minor fractions collected at about 7.69-8.20 min. was confirmed by ¹H-¹H through bond correlation, ¹H-¹³C HMBC and F-C6 coupling in ¹³C NMR (125.75 MHz, CD₃OD) (δ 152.5 ppm, d, J=242 Hz, C6) to be the isomer of the F-atom at C6 (C4:C6 about 3:1 based on preparative HPLC % area of the UV trace); ¹H NMR (500 MHz, CD₃OD) δ 8.04 (dd, J=8.55, 5.49, 2H), 7.59 (d, J=8.85, 1H), 7.38 (d, J=10.07, 1H), 7.25 (t, J=8.70, 2H), 4.40 (q, J=7.17, 2H), 1.41 (t, J=7.17, 3H). ¹⁹F NMR (470.45 MHz, CD₃OD) δ −112.29, −138.52. LC/MS were performed by using Shimadzu-VP instrument with UV detection at 220 nm and Waters Micromass. HPLC method: Solvent A=10% MeOH-90% H₂O—0.1% TFA, Solvent B=90% MeOH-10% H₂O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=319.14, HPLC R_t=1.798 min. (Alternatively, the two isomers were separated after the ester hydrolysis by Shimadzu-VP preparative reverse phase HPLC using the same method as above but with Start % B=40).

Preparation of 4-fluoro-2-(4-fluorophenyl)-5-hydroxybenzofuran-3-carboxylic acid

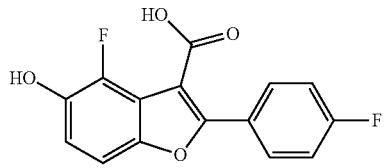 [SMILES: O=C(O)c1c(-c2ccc(F)cc2)oc2ccc(O)c(F)c12]

To a mixture of ethyl 4-fluoro-2-(4-fluorophenyl)-5-hydroxybenzofuran-3-carboxylate (108.9 mg, 0.342 mmol) in a mixture of MeOH (2 mL)/THF (2 mL) at r.t. under $N_2$ was added sodium hydroxide (1.0 mL, 1.0 mmol) (1 M aq.). The mixture was stirred at 100° C. for 1.5 hours. The mixture was cooled to r.t., added with 1.5 ml 1N HCl, and then added 10 ml $H_2O$. The white precipitates were filtered and washed with 3×2 ml $H_2O$ and dried (73 mg). $^1$H NMR (500 MHz, $CD_3OD$) δ 7.98 (m, 2H), 7.25 (t overlapping with dd, 2H), 7.24 (dd, 1H), 7.02 (t, J=8.39, 1H). LC/MS were performed by using Shimadzu-VP instrument with UV detection at 220 nm and Waters Micromass. HPLC method: Solvent A=10% MeOH-90% $H_2O$—0.1% TFA, Solvent B=90% MeOH-10% $H_2O$—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z $(M+H)^+$=291.01, HPLC $R_t$=1.478 min.

Preparation of 4-fluoro-2-(4-fluorophenyl)-5-hydroxy-N-methylbenzofuran-3-carboxamide

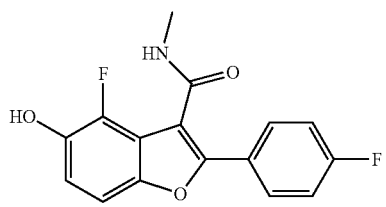 [SMILES: CNC(=O)c1c(-c2ccc(F)cc2)oc2ccc(O)c(F)c12]

To a mixture of 4-fluoro-2-(4-fluorophenyl)-5-hydroxybenzofuran-3-carboxylic acid (73 mg, 0.252 mmol), methylamine, HCl (25.5 mg, 0.377 mmol), HOBT hydrate (65.5 mg, 0.428 mmol) and EDC hydrochloride (87 mg, 0.453 mmol) at r.t. under $N_2$ was added N,N-diisopropylethylamine (0.220 mL, 1.258 mmol). The mixture was stirred at r.t. for 16 hours. After concentration, the mixture was added with 5 ml 1N HCl, and then 14 ml $H_2O$. The white solid was filtered and washed with 3×5 ml $H_2O$ and dried (64 mg). $^1$H NMR (500 MHz, $CD_3OD$) δ 7.89 (dd, J=8.09, 5.34, 2H), 7.25 (t overlapping with dd, 2H), 7.23 (dd, 1H), 6.99 (t, J=8.55, 1H), 2.96 (s, 3H). LC/MS were performed by using Shimadzu-VP instrument with UV detection at 220 nm and Waters Micromass. HPLC method: Solvent A=10% MeOH-90% $H_2O$—0.1% TFA, Solvent B=90% MeOH-10% $H_2O$—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z $(M+H)^+$=304.06, HPLC $R_t$=1.262 min.

Preparation of 4-fluoro-2-(4-fluorophenyl)-3-(methylcarbamoyl)benzofuran-5-yl trifluoromethanesulfonate

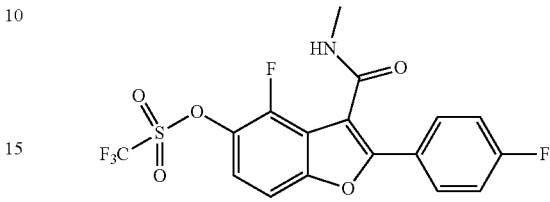

To a white suspension of 4-fluoro-2-(4-fluorophenyl)-5-hydroxy-N-methylbenzofuran-3-carboxamide (64 mg, 0.211 mmol) in $CH_2Cl_2$ (2 mL) at r.t. under $N_2$ was added triethylamine (0.059 mL, 0.422 mmol). The mixture was cooled to 0° C., and then added 1,1,1-trifluoro-N-phenyl-N-(trifluoromethylsulfonyl)methanesulfonamide (113 mg, 0.317 mmol). The mixture was then stirred at r.t. (the white suspension turned into a light yellow solution after stirring for about 10 min) for 2 hours 35 min. The mixture was left standing at r.t. overnight, and then evaporated. The residue was cooled in an ice-water bath, added with 2 ml $H_2O$. The solids were filtered and washed with 3×2 ml $H_2O$, and dried (94 mg). $^1$H NMR (500 MHz, $CD_3OD$) δ 7.95 (m, 2H), 7.59 (dd, J=9.00, 1.00, 1H), 7.50 (dd, J=9.00, 7.50, 1H), 7.30 (t, J=8.55, 2H), 2.99 (s, 3H). LC/MS were performed by using Shimadzu-VP instrument with UV detection at 220 nm and Waters Micromass. HPLC method: Solvent A=10% MeOH-90% $H_2O$—0.1% TFA, Solvent B=90% MeOH-10% $H_2O$—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z $(M+H)^+$=436.04, HPLC $R_t$=1.678 min.

Preparation of methyl 5-(4-fluoro-2-(4-fluorophenyl)-3-(methylcarbamoyl)benzofuran-5-yl)-2-methoxy-4-methylbenzoate

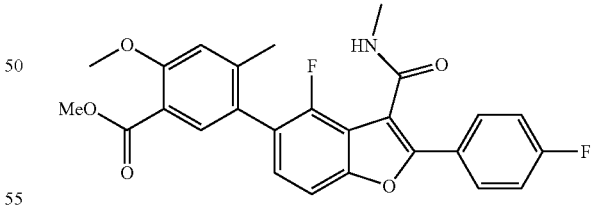

A mixture of the above prepared 4-fluoro-2-(4-fluorophenyl)-3-(methylcarbamoyl)benzofuran-5-yl trifluoromethanesulfonate (assumed 0.211 mmol), methyl 2-methoxy-4-methyl-5-(4,4,5,5-tetramethyl-1,3,2-dioxaborolan-2-yl)benzoate (0.078 g, 0.253 mmol), $(Ph_3P)_4Pd$ (0.024 g, 0.021 mmol) and cesium carbonate (0.103 g, 0.317 mmol) in a mixture of $H_2O$ (0.2 mL)/1,4-dioxane (1 mL) was stirred at 95° C. for 2 hours 30 min. The mixture was left standing at r.t. overnight. The mixture was diluted with 3.5 ml 1,4-dioxane, filtered through a Whatman PVDF 0.45 um disk (with 3×1 ml washing). The filtrate was concentrated. The mixture was added with 3.5 ml 1N HCl, and then 6 ml H$_2$O (yellow solid deposited on the wall of the flask). The aqueous was decanted, and the residue washed with 3×2 ml H$_2$O and dried. LC/MS were performed by using Shimadzu-VP instrument with UV detection at 220 nm and Waters Micromass. HPLC method: Solvent A=10% MeOH-90% H$_2$O—0.1% TFA, Solvent B=90% MeOH-10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=466.27, HPLC R$_t$=1.708 min.

Preparation of 5-(4-fluoro-2-(4-fluorophenyl)-3-(methylcarbamoyl)benzofuran-5-yl)-2-methoxy-4-methylbenzoic acid

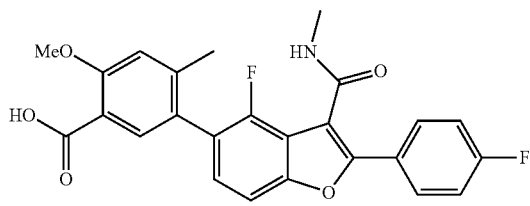 [SMILES: CNC(=O)c1c(-c2ccc(F)cc2)oc2ccc(-c3cc(C(=O)O)c(OC)cc3C)c(F)c12]

To the above prepared methyl 5-(4-fluoro-2-(4-fluorophenyl)-3-(methylcarbamoyl)benzofuran-5-yl)-2-methoxy-4-methylbenzoate (assumed 0.211 mmol) in a mixture MeOH (2 mL)/THF (2 mL) at r.t. under N$_2$ was added sodium hydroxide (0.84 mL, 0.84 mmol). The mixture was stirred at r.t. for 24 hours. The mixture was added with 2 ml 1N HCl, and concentrated until off white solids formed. The mixture was added with 5 ml H$_2$O, the solids filtered and washed with 3×2 ml H$_2$O and dried (75.1 mg). $^1$H NMR (500 MHz, CD$_3$OD) δ 7.95 (m, 2H), 7.73 (s, 1H), 7.51 (d, J=8.24, 1H), 7.30-7.25 (t overlapping with m, 3H), 7.13 (s, 1H), 3.99 (s, 3H), 2.96 (s, 3H), 2.28 (s, 3H). LC/MS were performed by using Shimadzu-VP instrument with UV detection at 220 nm and Waters Micromass. HPLC method: Solvent A=10% MeOH-90% H$_2$O—0.1% TFA, Solvent B=90% MeOH-10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=452.23, HPLC R$_t$=1.582.

The following intermediates were prepared in a similar manner as described.

Methyl 3-fluoro-5-(4-fluoro-2-(4-fluorophenyl)-3-(methylcarbamoyl)benzofuran-5-yl)-4-methylbenzoate

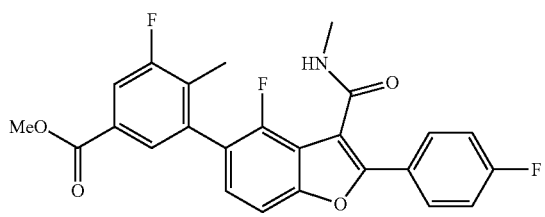 [SMILES: CNC(=O)c1c(-c2ccc(F)cc2)oc2ccc(-c3cc(C(=O)OC)cc(F)c3C)c(F)c12]

LC/MS were performed by using Shimadzu-VP instrument with UV detection at 220 nm and Waters Micromass. HPLC method: Solvent A=10% MeOH-90% H$_2$O—0.1% TFA, Solvent B=90% MeOH-10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=454.08, HPLC R$_t$=1.838 min.

3-Fluoro-5-(4-fluoro-2-(4-fluorophenyl)-3-(methylcarbamoyl)benzofuran-5-yl)-4-methylbenzoic acid

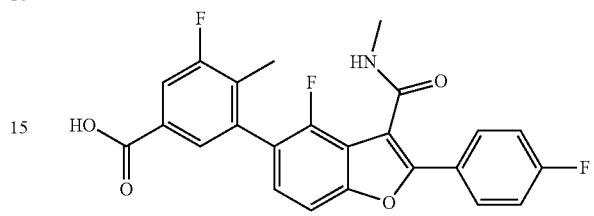

$^1$H NMR (500 MHz, CD$_3$OD) δ 7.96 (m, 2H), 7.76 (s, 1H), 7.75-7.73 (d, 1H), 7.56 (d, J=8.24, 1H), 7.33-7.28 (t overlapping with m, 3H), 2.96 (s, 3H), 2.20 (s, 3H). LC/MS were performed by using Shimadzu-VP instrument with UV detection at 220 nm and Waters Micromass. HPLC method: Solvent A=10% MeOH-90% H$_2$O—0.1% TFA, Solvent B=90% MeOH-10% H$_2$O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=440.09, HPLC R$_t$=1.720.

The following acid intermediate was prepared by either one of the methods shown below in a similar manner as described.

3-(4-Fluoro-2-(4-fluorophenyl)-3-(methylcarbamoyl)benzofuran-5-yl)-4-methylbenzoic acid

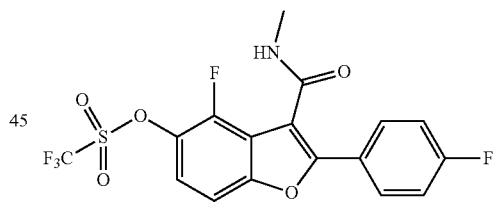

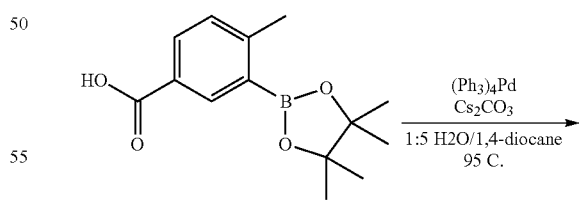

Or

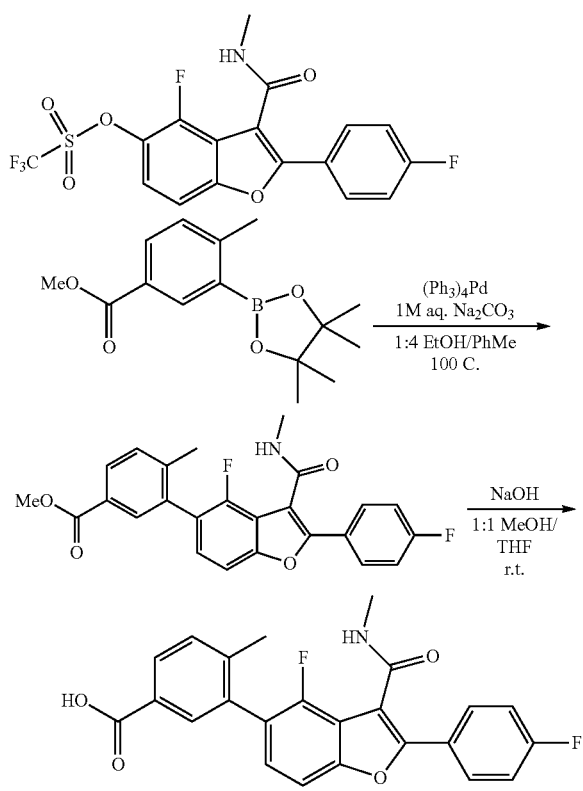

LC/MS were performed by using Shimadzu-VP instrument with UV detection at 220 nm and Waters Micromass. HPLC method: Solvent A=10% MeOH-90% H₂O—0.1% TFA, Solvent B=90% MeOH-10% H₂O—0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)⁺=422.19, HPLC R$_t$=1.653 min.

Synthesis of tert-butyl 3-(3-(4-fluoro-2-(4-fluorophenyl)-3-(methylcarbamoyl)benzofuran-5-yl)-4-methylbenzamido)-3-(pyrimidin-2-yl)azetidine-1-carboxylate

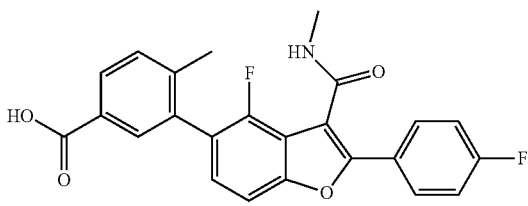 [SMILES: CNC(=O)c1c(-c2ccc(F)cc2)oc2ccc(-c3cc(C(=O)O)ccc3C)c(F)c12]

To a mixture of 3-(4-fluoro-2-(4-fluorophenyl)-3-(methylcarbamoyl)benzofuran-5-yl)-4-methylbenzoic acid (60 mg, 0.142 mmol) and tert-butyl 3-amino-3-(pyrimidin-2-yl)azetidine-1-carboxylate hydrochloride (40.8 mg, 0.142 mmol) in DMF (1 ml) was added PyBOP (74.1 mg, 0.142 mmol) and triethylamine (0.020 ml, 0.142 mmol). The reaction mixture was stirred overnight, and then diluted with water and extracted with EtOAc. The organic layer was further washed with water, dried over sodium sulphate and concentrated. The crude product was then purified by column chromatography (2% methanol in chloroform) to afford tert-butyl 3-(3-(4-fluoro-2-(4-fluorophenyl)-3-(methylcarbamoyl)benzofuran-5-yl)-4-methylbenzamido)-3-(pyrimidin-2-yl)azetidine-1-carboxylate Yield: 55 mg (59%). LCMS: (ES+) m/z observed=554.2 (M+H)⁺ of 4-fluoro-2-(4-fluorophenyl)-N-methyl-5-(2-methyl-5-(3-(pyrimidin-2-yl)azetidin-3-ylcarbamoyl)phenyl)benzofuran-3-carboxamide.

Column-ZORBAX SB C18 (50×4 6 mm-5 μm)
Mphase A: 10% MeOH—90% H₂O—0.1% TFA
Mphase B: 90% MeOH—10% H₂O—0.1% TFA
Flow: 1 ml/Min

| Time | % A | % B |
|------|-------|-------|
| 0.0  | 100.0 | 0     |
| 2    | 00.0  | 100.0 |
| 3    | 100.0 | 0.0   |

RT min: 2.1, wavelength: 220 nm

Synthesis of 4-fluoro-2-(4-fluorophenyl)-N-methyl-5-(2-methyl-5-(3-(pyrimidin-2-yl)azetidin-3-ylcarbamoyl)phenyl)benzofuran-3-carboxamide

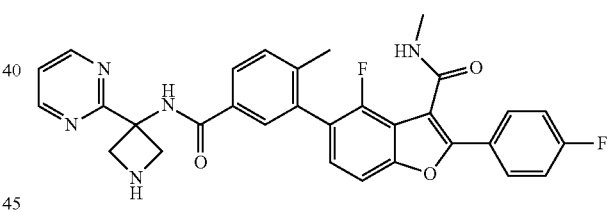

To a mixture of tert-butyl 3-(3-(4-fluoro-2-(4-fluorophenyl)-3-(methylcarbamoyl)benzofuran-5-yl)-4-methylbenzamido)-3-(pyrimidin-2-yl)azetidine-1-carboxylate (55 mg, 0.084 mmol) in MeOH (0.5 ml) in a 10 ml round-bottomed flask was added a solution of HCl in ether (0.021 ml, 0.084 mmol, 4 N). The mixture was stirred at room temperature for 30 min. After which time, no starting material was observed by LCMS. The reaction mixture was concentrated, and the crude residue was diluted with water and washed with ethyl acetate (10 ml). The aq. layer was basified with solid NaHCO₃, and back extracted with ethyl acetate (3×10 ml). The combined the organic layers were washed with brine solution (3×15 ml), dried with Na₂SO₄, filtered and concentrated. The product obtained was re-crystallized from ethyl acetate ether. Yield: 42 mg (90%). ¹H NMR (400 MHz, DMSO-d₆): δ 9.38 (s, 1H), 8.80 (d, J=4.8 Hz, 2H), 8.71 (broad d, J=4.4 Hz, 1H), 7.96-7.86 (m, 4H), 7.66 (d, J=8.4 Hz, 2H), 7.48-7.35 (m, 5H), 4.10 (d, J=8.8 Hz, 2H), 3.84 (d, J=8.4 Hz, 2H), 2.80 (d, J=4.8 Hz, 3H), 2.23 (s, 3H). ¹⁹FNMR (376.47 MHz, DMSO-d₆): δ −110.43, −121.44. LCMS: (ES+) m/z=554.2 (M+H)⁺

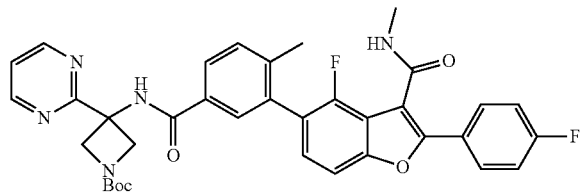 [SMILES: CNC(=O)c1c(-c2ccc(F)cc2)oc2ccc(-c3cc(C(=O)NC4(c5ncccn5)CN(C(=O)OC(C)(C)C)C4)ccc3C)c(F)c12]

Column-ZORBAX SB C18 (50×4 6 mm-5 μm)
Mphase A: 10% MeOH—90% H₂O—0.1% TFA
Mphase B: 90% MeOH—10% H₂O—0.1% TFA
Flow: 1 ml/Min

| Time | % A | % B |
|---|---|---|
| 0.0 | 100.0 | 0 |
| 2 | 00.0 | 100.0 |
| 3 | 100.0 | 0.0 |

RT min: 1.69, wavelength: 220 nm
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 6.90
Wavelength: 220 nm, RT min: 6.90
HPLC Method: XBridge phenyl (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 8.13
Wavelength: 220 nm, RT min: 8.13

Synthesis 4-fluoro-2-(4-fluorophenyl)-N-methyl-5-(2-methyl-5-(1-methyl-3-(pyrimidin-2-yl)azetidin-3-ylcarbamoyl)phenyl)benzofuran-3-carboxamide

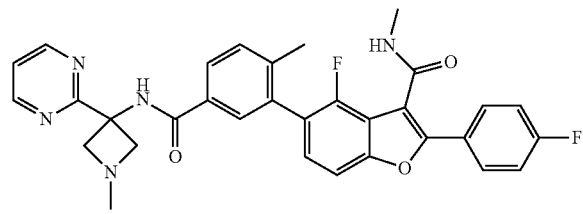 [SMILES: CNC(=O)c1c(-c2ccc(F)cc2)oc2ccc(-c3cc(C(=O)NC4(c5ncccn5)CN(C)C4)ccc3C)c(F)c12]

To a colorless suspension of 4-fluoro-2-(4-fluorophenyl)-N-methyl-5-(2-methyl-5-(3-(pyrimidin-2-yl)azetidin-3-yl-carbamoyl)phenyl)benzofuran-3-carboxamide (25 mg, 0.045 mmol) and paraformaldehyde (2.034 mg, 0.068 mmol) in MeOH (1 ml) in a 5 ml round-bottomed flask was added sodium cyanoborohydride (4.26 mg, 0.068 mmol). The reaction mixture was stirred at room temperature for 1 hour and concentrated to remove methanol. The crude residue was diluted with ethyl acetate (10 ml), and washed with sat. NH₄Cl solution. The organic solution was dried over Na₂SO₄, filtered and concentrated. The product was purified by Prep-HPLC and obtained as TFA salt. Yield 19 mg (74%).
¹H NMR (400 MHz, CD₃OD at 55° C.): δ 8.92 (s, 1H), 7.97-7.92 (m, 3H), 7.86 (d, J=1.6 Hz, 1H), 7.54-7.50 (m, 3H), 7.32-7.25 (m, 3H), 5.1-4.8 (broad m, 4H), 3.21 (s, 3H), 2.96 (s, 3H), 2.31 (s, 3H). ¹⁹F NMR (376.57 MHz, CD₃OD): δ −77.03 (TFA), −112.14, −122.86. LCMS: (ES+) m/z=568.2 (M+H)⁺ Column-ZORBAX SB C18 (50×4 6 mm-5 μm)
Mphase A: 10% MeOH—90% H₂O—0.1% TFA
Mphase B: 90% MeOH—10% H₂O—0.1% TFA
Flow: 1 ml/Min

| Time | % A | % B |
|---|---|---|
| 0.0 | 100.0 | 0 |
| 2 | 00.0 | 100.0 |
| 3 | 100.0 | 0.0 |

RT min: 1.7, wavelength: 220 nm
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 7.06
Wavelength: 220 nm, RT min: 7.06
HPLC Method: XBridge phenyl (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.10
Wavelength: 220 nm, RT min: 9.10
Preparative HPLC Method
Column: Sunfire C18 (19×150×5μ)
Mobile Phase: 0.05% TFA (A), MeCN (B)

| Gradient: | | |
|---|---|---|
| Time | Flow | B % |
| 0 | 18 ml/min | 20 |
| 12 | 18 ml/min | 100 |

RT: 5.1 min

Synthesis of tert-butyl 3-(5-(4-fluoro-2-(4-fluorophenyl)-3-(methylcarbamoyl)benzofuran-5-yl)-2-methoxy-4-methylbenzamido)-3-(pyrimidin-2-yl)azetidine-1-carboxylate

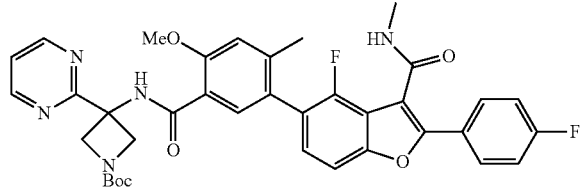 [SMILES: CNC(=O)c1c(-c2ccc(F)cc2)oc2ccc(-c3cc(C(=O)NC4(c5ncccn5)CN(C(=O)OC(C)(C)C)C4)c(OC)cc3C)c(F)c12]

To a mixture of 5-(4-fluoro-2-(4-fluorophenyl)-3-(methylcarbamoyl)benzofuran-5-yl)-2-methoxy-4-methylbenzoic acid (50 mg, 0.111 mmol) and tert-butyl 3-amino-3-(pyrimidin-2-yl)azetidine-1-carboxylate hydrochloride (31.8 mg, 0.111 mmol) in DMF (1 ml) in a 25 ml round-bottomed flask was added PyBOP (69.2 mg, 0.133 mmol) and then triethylamine (0.046 ml, 0.332 mmol). The reaction mixture was stirred overnight, and then diluted with water and extracted with EtOAc. The organic layer was further washed with water, dried over sodium sulphate and concentrated. The crude product was then purified by column chromatography (2% methanol in chloroform) to afford tert-butyl 3-(5-(4-fluoro-2-(4-fluorophenyl)-3-(methylcarbamoyl)benzofuran-5-yl)-2-methoxy-4-methylbenzamido)-3-(pyrimidin-2-yl)azetidine-1-carboxylate. Yield: 40 mg (53%). LCMS: (ES+) m/z observed=584.2 (M+H)$^+$ of 4-fluoro-2-(4-fluorophenyl)-5-(4-methoxy-2-methyl-5-(3-(pyrimidin-2-yl)azetidin-3-ylcarbamoyl)phenyl)-N-methylbenzofuran-3-carboxamide Column-PUROSPHER@ star RP-18 (55×4 mm-3 μm)
Buffer: 20 Mm NH$_4$OAC in water
Mobile Phase A: Buffer:MeCN (90:10)
Mobile Phase B: MeCN:Buffer (90:10)
Flow: 2.5 ml/Min

| Time | % A | % B |
| --- | --- | --- |
| 0.0 | 100.0 | 0.00 |
| 2 | 00.0 | 100.0 |
| 2.5 | 00.0 | 100.0 |
| 3 | 100.0 | 00.0 |

RT min: 2.7, wavelength: 220 nm

Synthesis 4-fluoro-2-(4-fluorophenyl)-5-(4-methoxy-2-methyl-5-(3-(pyrimidin-2-yl)azetidin-3-ylcarbamoyl)phenyl)-N-methylbenzofuran-3-carboxamide

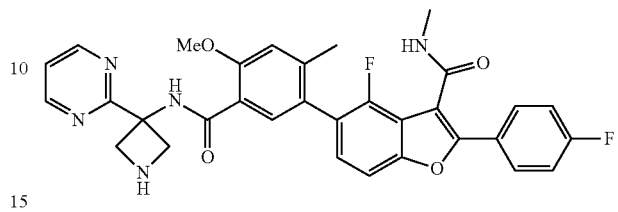

To a clear solution of tert-butyl 3-(5-(4-fluoro-2-(4-fluorophenyl)-3-(methylcarbamoyl)benzofuran-5-yl)-2-methoxy-4-methylbenzamido)-3-(pyrimidin-2-yl)azetidine-1-carboxylate (40 mg, 0.059 mmol) MeOH (0.5 ml) in a 10 mL round-bottomed flask was added a solution of HCl in ether (0.146 ml, 0.585 mmol, 4 N). The mixture was stirred at room temperature for 30 min. After which time, no starting material was observed by LCMS analysis. The reaction mixture was concentrated, and the residue diluted with water and extracted with ethyl acetate (10 ml). The aqueous layer was basified with solid NaHCO$_3$ and extracted with ethyl acetate (3×10 ml). The combined the organic extracts were washed with brine solution (3×15 ml), dried over Na$_2$SO$_4$, filtered and concentrated. The product was purified by Prep-HPLC and obtained as TFA salt. Yield: 18 mg (53%).

$^1$H NMR (400 MHz, DMSO-d$_6$): δ 10.06 (s, 1H), 9.21 (b s, 2H), 9.03 (d, J=4.8 Hz, 2H), 8.70 (d, J=4.8 Hz, 1H), 7.93 (m, 2H), 7.88 (s, 1H), 7.65-7.62 (m, 2H), 7.43 (t, J=8.8 Hz, 2H), 7.33 (m, 1H), 7.30 (s, 1H), 4.71 (m, 2H), 4.51 (m, 2H), 4.13 (s, 3H), 2.80 (d, J=4.8 Hz, 3H), 2.27 (s, 3H). $^{19}$F NMR (376.47 MHz, DMSO-d$_6$): δ −73.55 (TFA), −110.39, −121.65. LCMS: (ES+) m/z observed=584.0 (M+H)$^+$ Column-Ascentis Express C18 (5×4 6 mm-5 μm)
Mphase A: 2% MeCN—98% H$_2$O—10 mM NH$_4$COOH
Mphase B: 98% MeCN—2% H$_2$O—10 mM NH$_4$COOH
Flow: 1 ml/Min

| Time | % A | % B |
| --- | --- | --- |
| 0.0 | 100.0 | 0 |
| 1.5 | 0.0 | 100.0 |
| 3.2 | 0.0 | 100.0 |

RT min: 1.76, wavelength: 220 nm
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 7.31
Wavelength: 220 nm, RT min: 7.31
HPLC Method: XBridge phenyl (4.6×150)mm, 3.5 micron
Buffer: 0.05% TFA in water pH 2.5

Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 8.64
Wavelength: 220 nm, RT min: 8.64
Preparative HPLC Method
Column: XBridege phenyl (19×250×5μ)
Mobile Phase: 0.05% TFA (A), MeCN (B)

| Gradient: | | |
| --- | --- | --- |
| Time | Flow | B % |
| 0 | 15 ml/min | 20 |
| 10 | 15 ml/min | 60 |

RT: 9.50 min

Synthesis 4-fluoro-2-(4-fluorophenyl)-5-(4-methoxy-2-methyl-5-(1-methyl-3-(pyrimidin-2-yl)azetidin-3-ylcarbamoyl)phenyl)-N-methylbenzofuran-3-carboxamide

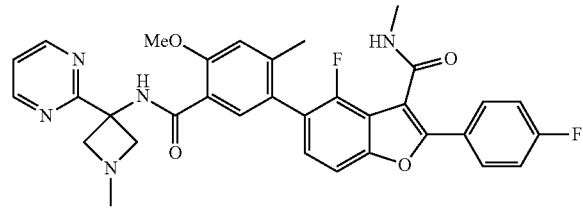 [SMILES: CNC(=O)c1c(-c2ccc(F)cc2)oc2ccc(-c3cc(C(=O)NC4(c5ncccn5)CN(C)C4)c(OC)cc3C)c(F)c12]

To a colorless suspension of 4-fluoro-2-(4-fluorophenyl)-5-(4-methoxy-2-methyl-5-(3-(pyrimidin-2-yl)azetidin-3-ylcarbamoyl)phenyl)-N-methylbenzofuran-3-carboxamide (30 mg, 0.051 mmol) and paraformaldehyde (2.315 mg, 0.077 mmol) in MeOH (1 ml) in a 5 mL round-bottomed flask was added sodium cyanoborohydride (4.85 mg, 0.077 mmol) The reaction mixture was stirred at room temperature for 1 h. and concentrated to remove methanol. The residue was diluted with ethyl acetate (10 ml), washed with sat. NH$_4$Cl solution. The organic solution was dried over Na$_2$SO$_4$, filtered and concentrated. The product was purified by Prep-HPLC and obtained as a TFA salt. Yield 10 mg (33%). $^1$H NMR (400 MHz, CD$_3$OD at 55° C.): δ 9.04 (d, J=4.8 Hz, 2H), 8.08 (b s, 1H), 7.95 (m, 2H), 7.59 (t, J=4.8 Hz, 1H), 7.52 (d, J=8.8 Hz, 1H), 7.29-7.23 (m, 4H), 5.20 (d, J=11.6 Hz, 2H), 4.71 (d, J=10.8 Hz, 2H), 4.20 (s, 3H), 3.26 (s, 3H), 2.96 (s, 3H), 2.32 (s, 3H). $^{19}$F NMR (376.57 MHz, CD$_3$OD): δ −77.01 (TFA), −112.22, −122.88. LCMS: (ES+) m/z observed=599.2 (M+2H)$^+$ Column-ZORBAX SB C18 (50×4 6 mm-5 μm)
Mphase A: 10% MeOH—90% H$_2$O—0.1% TFA
Mphase B: 90% MeOH—10% H$_2$O—0.1% TFA
Flow: 1 ml/Min

| Time | % A | % B |
| --- | --- | --- |
| 0.0 | 100.0 | 0 |
| 2 | 00.0 | 100.0 |
| 3 | 100.0 | 0.0 |

RT min: 1.78, wavelength: 220 nm
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 7.42
Wavelength: 220 nm, RT min: 7.42
HPLC Method: XBridge phenyl (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
| --- | --- |
| 0 | 10 |
| 12 | 100 |
| 15 | 100 |

Wavelength: 254 nm, RT min: 9.86
Wavelength: 220 nm, RT min: 9.86
Preparative HPLC Method
Column: Sunfire C18 (19×150×5μ)
Mobile Phase: 0.05% TFA (A), MeCN (B)

| Gradient: | | |
| --- | --- | --- |
| Time | Flow | B % |
| 0 | 18 ml/min | 20 |
| 12 | 18 ml/min | 45 |

RT: 9.9 min

Synthesis of tert-butyl 3-(3-fluoro-5-(4-fluoro-2-(4-fluorophenyl)-3-(methylcarbamoyl)benzofuran-5-yl)-4-methylbenzamido)-3-(pyrimidin-2-yl)azetidine-1-carboxylate

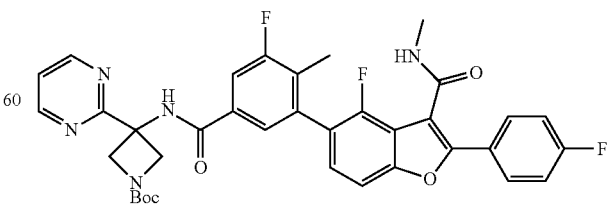

To a mixture of 3-fluoro-5-(4-fluoro-2-(4-fluorophenyl)-3-(methylcarbamoyl)benzofuran-5-yl)-4-methylbenzoic acid (50 mg, 0.114 mmol) and tert-butyl 3-amino-3-(pyrimidin-2-yl)azetidine-1-carboxylate hydrochloride (35.9 mg, 0.125 mmol) in DMF (1 ml) in a 25 ml round-bottomed flask was added PyBop (77 mg, 0.148 mmol) and then triethylamine (0.032 ml, 0.228 mmol). The reaction mixture was stirred overnight, and then diluted with water and extracted with EtOAc. The organic layer was further washed with water, dried over sodium sulphate and concentrated. The crude product was then purified by column chromatography (2% methanol in chloroform) to afford tert-butyl 3-(3-fluoro-5-(4-fluoro-2-(4-fluorophenyl)-3-(methylcarbamoyl)benzofuran-5-yl)-4-methylbenzamido)-3-(pyrimidin-2-yl)azetidine-1-carboxylate. Yield: 40 mg (52.4%). LCMS: (ES+) m/z observed=572.2 (M+H)+ of 4-fluoro-5-(3-fluoro-2-methyl-5-(3-(pyrimidin-2-yl)azetidin-3-ylcarbamoyl)phenyl)-2-(4-fluorophenyl)-N-methylbenzofuran-3-carboxamide Column-PUROSPHER@ star RP-18 (55×4 mm-3 µm).
Buffer: 20 mM NH$_4$OAC in water
Mobile Phase A: Buffer:MeCN (90:10)
Mobile Phase B: MeCN:Buffer (90:10)
Flow: 2.5 ml/Min

| Time | % A | % B |
|---|---|---|
| 0.0 | 100.0 | 0.00 |
| 2 | 00.0 | 100.0 |
| 2.5 | 00.0 | 100.0 |
| 3 | 100.0 | 00.0 |

RT min: 2.1, wavelength: 220 nm

Synthesis 4-fluoro-5-(3-fluoro-2-methyl-5-(3-(pyrimidin-2-yl)azetidin-3-ylcarbamoyl)phenyl)-2-(4-fluorophenyl)-N-methylbenzofuran-3-carboxamide

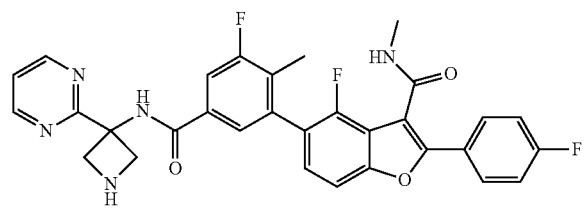 [SMILES: CNC(=O)c1c(-c2ccc(F)cc2)oc2ccc(-c3cc(C(=O)NC4(c5ncccn5)CNC4)cc(F)c3C)c(F)c12]

To a solution of tert-butyl 3-(3-fluoro-5-(4-fluoro-2-(4-fluorophenyl)-3-(methylcarbamoyl)benzofuran-5-yl)-4-methylbenzamido)-3-(pyrimidin-2-yl)azetidine-1-carboxylate (40 mg, 0.060 mmol) in methanol (0.5 ml) in a 10 ml round-bottomed flask was added a solution of HCl in ether (0.199 ml, 0.596 mmol, 3 N). The reaction mixture was stirred at room temperature for 30 min. After which time, no starting material was observed by LCMS analysis. The reaction mixture was concentrated, diluted with water and extracted with ethyl acetate (10 ml). The aqueous layer was basified with solid NaHCO$_3$ and extracted with ethyl acetate (3×10 ml). The combined organic extracts were washed with brine solution (3×15 ml), dried over Na$_2$SO$_4$, filtered and concentrated. The product was purified by Prep-HPLC and obtained as TFA salt. Yield: 20 mg (59%). $^1$H NMR (400 MHz, DMSO-d$_6$): δ 9.81 (s, 1H), 9.20 (b s, 2H), 8.91 (d, J=4.8 Hz, 2H), 8.72 (d, J=4.8 Hz, 1H), 7.94 (m, 2H), 7.78 (d, 1H), 7.77 (s, 1H), 7.71 (d, J=8.8 Hz, 1H), 7.53 (t, J=4.8 Hz, 1H), 7.46-7.38 (m, 3H), 4.62 (m, 2H), 4.43 (m, 2H), 2.81 (d, J=4.8 Hz, 3H), 2.16 (s, 3H). $^{19}$F NMR (376.57 MHz, DMSO-d$_6$): δ −73.64 (TFA), −110.21, −114.41, −121.40.

LCMS: (ES+) m/z=572.2 (M+H)+
Column-ZORBAX SB C18 (50×4 6 mm-5 µm)
Mphase A: 10% MeOH—90% H$_2$O—0.1% TFA
Mphase B: 90% MeOH—10% H$_2$O—0.1% TFA
Flow: 1 ml/Min

| Time | % A | % B |
|---|---|---|
| 0.0 | 100.0 | 0 |
| 2 | 00.0 | 100.0 |
| 3 | 100.0 | 0.0 |

RT min: 1.75, wavelength: 220 nm
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 7.14
Wavelength: 220 nm, RT min: 7.14
HPLC Method: XBridge phenyl (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 8.39
Wavelength: 220 nm, RT min: 8.39
Preparative HPLC Method
Column: XBridge phenyl (19×250×5µ)
Mobile Phase: 0.05% TFA (A), MeCN (B)

| Gradient: | | |
|---|---|---|
| Time | Flow | B % |
| 0 | 15 ml/min | 20 |
| 10 | 15 ml/min | 60 |

RT: 9.00 min

Synthesis 4-fluoro-5-(3-fluoro-2-methyl-5-(1-methyl-3-(pyrimidin-2-yl)azetidin-3-ylcarbamoyl)phenyl)-2-(4-fluorophenyl)-N-methylbenzofuran-3-carboxamide

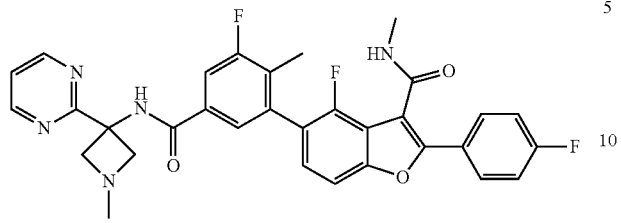

To a colorless suspension of 4-fluoro-5-(3-fluoro-2-methyl-5-(3-(pyrimidin-2-yl)azetidin-3-ylcarbamoyl)phenyl)-2-(4-fluorophenyl)-N-methylbenzofuran-3-carboxamide (30 mg, 0.052 mmol) and paraformaldehyde (2.364 mg, 0.079 mmol) in MeOH (1 ml) in a 5 mL round-bottomed flask was added sodium cyanoborohydride (4.95 mg, 0.079 mmol). The reaction mixture was stirred at room temperature for 1 hr., and then concentrated to remove methanol and diluted with ethyl acetate (10 ml). The organic layer was washed with sat. $NH_4Cl$ solution, dried over $Na_2SO_4$, filtered and concentrated. The product was purified by Prep-HPLC and obtained as TFA salt. Yield: 10 mg (33%). $^1H$ NMR (400 MHz, $CD_3OD$ at 55° C.): δ 8.93 (d, J=4.8 Hz, 2H), 7.9-7.94 (m, 2H), 7.73-7.72 (m, 2H), 7.56 (d, J=8.4 Hz, 1H), 7.52 (t, J=4.8 Hz, 1H), 7.35-7.26 (m, 3H), around 4.54 (m, 4H, obscured by solvent peak), 3.18 (s, 3H), 2.96 (s, 3H), 2.22 (s, 3H). $^{19}F$ NMR (376.47 MHz, $CD_3OD$): δ −76.99 (TFA), −112.03, −116.00, −122.73. LCMS: (ES+) m/z observed=587.2 $(M+2H)^+$ Column-ZORBAX SB C18 (50×4 6 mm-5 μm)
Mphase A: 10% MeOH-90% $H_2O$—0.1% TFA
Mphase B: 90% MeOH-10% $H_2O$—0.1% TFA
Flow: 1 ml/Min

| Time | % A | % B |
|---|---|---|
| 0.0 | 100.0 | 0 |
| 2 | 00.0 | 100.0 |
| 3 | 100.0 | 0.0 |

RT min: 1.73, wavelength: 220 nm
HPLC Method: SUNFIRE C18 (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 7.28
Wavelength: 220 nm, RT min: 7.28
HPLC Method: XBridge phenyl (4.6×150)mm, 3.5 micron
Buffer: 0.05% TFA in water pH 2.5
Mobile Phase A: Buffer:MeCN (95:5)
Mobile Phase B: MeCN:Buffer (95:5)
Flow: 1 ml/min

| Time | B % |
|---|---|
| 0 | 10 |
| 12 | 100 |
| 15 | 100 |

Wavelength: 254 nm, RT min: 9.43
Wavelength: 220 nm, RT min: 9.43
Preparative HPLC Method
Column: Sunfire C18 (19×150×5μ)
Mobile Phase: 0.05% TFA (A), MeCN (B)

| Gradient: | | |
|---|---|---|
| Time | Flow | B % |
| 0 | 18 ml/min | 10 |
| 15 | 18 ml/min | 100 |

RT: 9.3 min

Biological Methods

HCV NS5B RdRp Cloning, Expression, and Purification.
The cDNA encoding the NS5B protein of HCV, genotype 1b, was cloned into the pET21a expression vector. The protein was expressed with an 18 amino acid C-terminal truncation to enhance the solubility. The E. coli competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM $MgCl_2$, 15 ug/mL deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 μm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, $MgCl_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp Enzyme Assay.
An on-bead solid phase homogeneous assay was used in a 384-well format to assess NS5B inhibitors (WangY-K, Rigat K, Roberts S, and Gao M (2006) Anal Biochem, 359: 106-111). The biotinylated oligo $dT_{12}$ primer was captured on streptavidin-coupled imaging beads (GE, RPNQ0261) by mixing primer and beads in 1X buffer and incubating at room temperature for three hours. Unbound primer was removed after centrifugation. The primer-bound beads were resuspended in 3X reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (10 µL) of water, 3X reaction mix, and enzyme in 3X assay buffer (60 mM Hepes buffer, pH 7.5, 7.5 mM $MgCl_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 µM $^3$H-UTP (0.3 µCi), 1.6 U/µL RNAse inhibitor, 7 nM NS5B enzyme, 0.01 mg/mL BSA, 1 mM DTT, and 0.33 µg/µL beads, 20 mM Hepes buffer, pH 7.5, 2.5 mM $MgCl_2$, 2.5 mM KCl, and 0.1% DMSO.

Reactions were allowed to proceed for 4 hours at 30° C. and terminated by the addition of 50 mM EDTA (10 µL). After incubating for at least 15 minutes, plates were read on an Amersham LEADseeker multimodality imaging system.

$IC_{50}$ values for compounds were determined using ten different [I]. $IC_{50}$ values were calculated from the inhibition using the four-parameter logistic formula $y=A+((B-A)/(1+((C/x)^D)))$, where A and B denote minimal and maximal % inhibition, respectively, C is the $IC_{50}$, D is hill slope and x represents compound concentration.

Cell Lines.

The cell lines used to evaluate compounds consist of a human hepatocyte derived cell line (Huh-7) that constitutively expresses a genotype 1b HCV replicon containing a Renilla luciferase reporter gene. These cells were maintained in Dulbecco's modified Eagle medium (DMEM) containing 10% FBS, 100 U/mL penicillin/streptomycin and 1.0 mg/mL G418.

HCV Replicon Luciferase Assay.

To evaluate compound efficacy, titrated compounds were transferred to sterile 384-well tissue culture treated plates, and the plates were seeded with HCV replicon cells (50 µL at a density of $2.4 \times 10^3$ cells/well) in DMEM containing 4% FBS (final DMSO concentration at 0.5%). After 3 days incubation at 37° C., cells were analyzed for Renilla Luciferase activity using the EnduRen substrate (Promega cat #E6485) according to the manufacturer's directions. Briefly, the EnduRen substrate was diluted in DMEM and then added to the plates to a final concentration of 7.5 µM. The plates were incubated for at least 1 h at 37° C. then read on a Viewlux Imager (PerkinElmer) using a luminescence program. The 50% effective concentration ($EC_{50}$) was calculated using the four-parameter logistic formula noted above.

To assess cytotoxicity of compounds, Cell Titer-Blue (Promega) was added to the EnduRen-containing plates and incubated for at least 4 hrs at 37° C. The fluorescence signal from each well was read using a Viewlux Imager. All $CC_{50}$ values were calculated using the four-parameter logistic formula.

Enzyme and replicon data for compound I is reported in Table 2.

TABLE 2

| Structure | $EC_{50}$ (µM) | $IC_{50}$ (µM) |
|---|---|---|
| 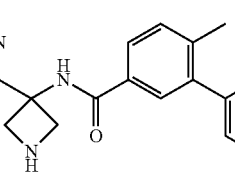 | 4.33 | |
| 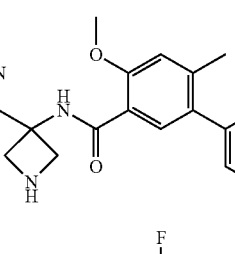 | 0.90 | −1.92 |
| 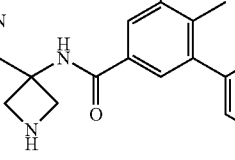 | 0.39 | 0.33 |
| 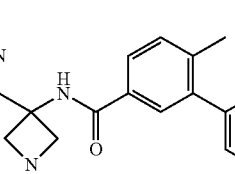 | 2.46 | 0.78 |

TABLE 2-continued

| Structure | EC$_{50}$ (μM) | IC$_{50}$ (μM) |
|---|---|---|
| 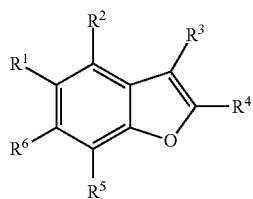 | 1.19 | −1.08 |
| 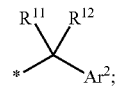 | 0.82 | 0.68 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula I where:
  $R^1$ is phenyl or pyridinyl and is substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy, and wherein the phenyl or pyridinyl is also substituted with 1 CON($R^9$)($R^{10}$) substituent;
  $R^2$ is hydrogen, halo, alkyl, or alkoxy;
  $R^3$ is cyano, alkoxycarbonyl, (cycloalkyl)oxycarbonyl, (alkylsulfonyl)aminocarbonyl, CON($R^{13}$)($R^{14}$), ($R^{13}$)($R^{14}$)NCONH, thiazolyl, tetrazolyl, triazolyl, or imidazolyl wherein the thiazolyl, tetrazolyl, triazolyl, or imidazolyl is substituted with 0-3 halo or alkyl substituents;
  $R^4$ is phenyl that is independently substituted with 0-2 halo, alkyl, or alkoxy or is para substituted with X—Ar$^1$;
  $R^5$ and $R^6$ are independently hydrogen, nitro, halo, alkyl, alkoxy, N($R^7$)($R^8$), or alkylsulfonyl;
  $R^7$ and $R^8$ are independently hydrogen, alkyl, cyanoalkyl, haloalkyl, (cycloalkyl)alkyl, cycloalkyl, hydroxyalkyl, alkoxyalkyl, alkylcarbonyl, alkoxycarbonyl, haloalkoxycarbonyl, alkylsulfonyl, alkylsulfonylalkyl, SO$_2$N($R^{15}$)($R^{16}$), or benzyl where said benzyl is substituted with 0-3 substituents selected from halo, alkyl, haloalkyl, alkoxy, haloalkoxy, carboxy, and alkoxycarbonyl;
  or N($R^7$)($R^8$) taken together is azetidinyl, pyrrolidinyl, piperidinyl, or piperazinyl, and is substituted with 0-2 substituents selected from alkyl, hydroxyalkyl, or hydroxy;
  $R^9$ is $R^{10}$ is hydrogen;
  $R^{11}$ and $R^{12}$ taken together with the carbon to which they are attached is azetidinyl substituted with 0-3 alkyl substituents;
  $R^{13}$ is hydrogen or alkyl;
  $R^{14}$ is hydrogen or alkyl;
  $R^{15}$ is hydrogen or alkyl;
  $R^{16}$ is hydrogen or alkyl;
  X is —O— or —NH—;
  Ar$^1$ is phenyl or para-halophenyl; and
  Ar$^2$ is phenyl, pyridinyl, pyrazinyl, pyrimidinyl, pyrazolyl, isoxazolyl, imidazolyl, oxazolyl, thiazolyl, oxadiazolyl, oxadiathiazolyl, triazolyl, or tetrazolyl, and is substituted with 0-3 substituents selected from halo, alkyl, or dialkylamino;
  or a pharmaceutically acceptable salt thereof.

2. A compound of claim 1 where $R^1$ is phenyl substituted with 0-3 substituents selected from the group consisting of halo and alkoxy, and is also substituted with 1 CON($R^9$)($R^{10}$) substituent;
  $R^2$ is hydrogen or halo;
  $R^3$ is CON($R^{13}$)($R^{14}$);
  $R^4$ is phenyl that is para substituted with halo;
  $R^5$ is hydrogen;
  $R^6$ is hydrogen, nitro, halo, alkyl, alkoxy, N($R^7$)($R^8$), or alkylsulfonyl;

Ar² is phenyl, pyridinyl, or pyrimidinyl, and is substituted with 0-3 substituents selected from halo or alkyl;
or a pharmaceutically acceptable salt thereof.

3. A compound of claim 2 wherein
R¹ is phenyl substituted with 2 substituents selected from the group consisting of halo, alkyl, and alkoxy, and is also substituted with 1 CON(R⁹)(R¹⁰) substituent; R² is halo; R³ is CONHMe; R⁴ is phenyl that is para substituted with halo; R⁵ is hydrogen; R⁶ is hydrogen; and Ar² is pyrimidinyl; or a pharmaceutically acceptable salt thereof.

4. A compound of claim 1 where R¹ is phenyl or pyridinyl wherein the phenyl or pyridinyl is substituted with 0-3 substituents selected from the group consisting of halo, alkyl, cycloalkyl, haloalkyl, hydroxyalkyl, alkoxyalkyl, alkoxy, cycloalkoxy, hydroxyalkyloxy, and alkoxyalkyloxy, and is also substituted with 1 CON(R⁹)(R¹⁰) substituent; or a pharmaceutically acceptable salt thereof.

5. A compound of claim 1 where R² is hydrogen or halo; or a pharmaceutically acceptable salt thereof.

6. A compound of claim 1 where R³ is CON(R¹³)(R¹⁴); or a pharmaceutically acceptable salt thereof.

7. A compound of claim 6 where R³ is CONHMe; or a pharmaceutically acceptable salt thereof.

8. A compound of claim 1 where R⁵ is hydrogen and R⁶ is hydrogen or N(R⁷)(R⁸); or a pharmaceutically acceptable salt thereof.

9. A compound of claim 1 where Ar² is phenyl, pyridinyl, pyrazinyl, or pyrimidinyl; or a pharmaceutically acceptable salt thereof.

10. A compound of claim 1 selected from the group consisting of

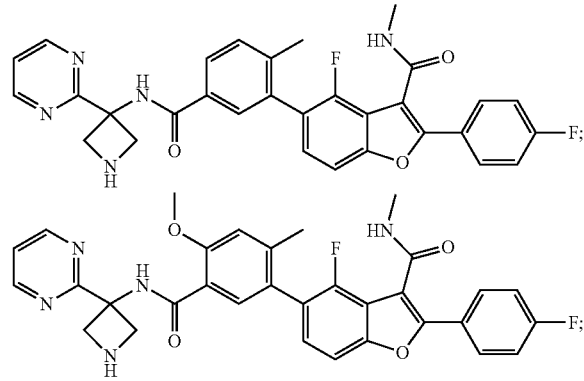

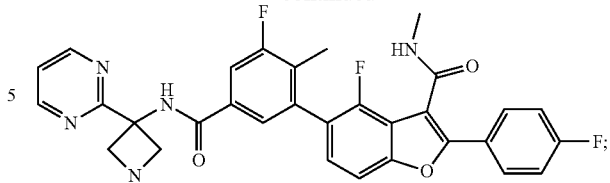

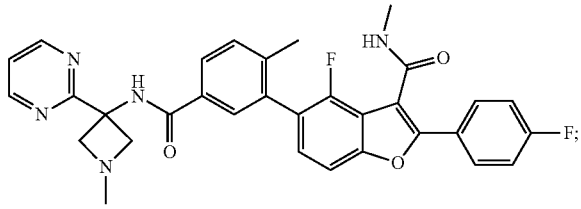

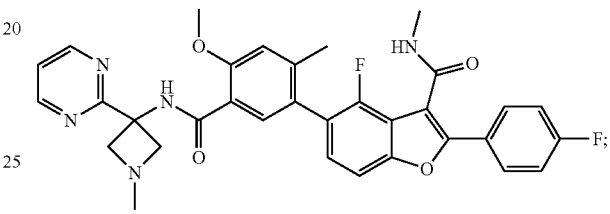

and

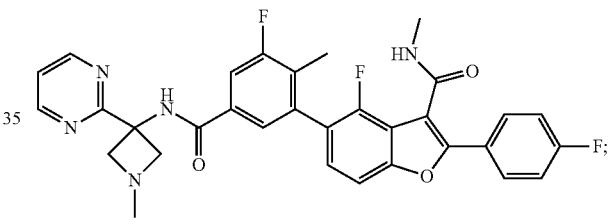

or a pharmaceutically acceptable salt thereof.

11. A composition comprising a compound of claim 1 or a pharmaceutically acceptable salt thereof and a pharmaceutically acceptable carrier.

12. A method of treating hepatitis C infection comprising administering a therapeutically effective amount of a compound of claim 1 to a patient.

* * * * *